US012569545B2

(12) United States Patent
Gu et al.

(10) Patent No.: US 12,569,545 B2
(45) Date of Patent: Mar. 10, 2026

(54) METHOD FOR TREATING AND/OR IMPROVING INFLAMMATORY INTESTINAL DISEASE

(71) Applicant: Tunghai University, Taichung (TW)

(72) Inventors: Yesong Gu, Taichung (TW); Woan-Ling Chen, Taichung (TW); Te-Hsin Chao, Taichung (TW)

(73) Assignee: Tunghai University, Taichung (TW)

( * ) Notice: Subject to any disclaimer, the term of this patent is extended or adjusted under 35 U.S.C. 154(b) by 364 days.

(21) Appl. No.: 18/323,328

(22) Filed: May 24, 2023

(65) Prior Publication Data

US 2024/0307513 A1 Sep. 19, 2024

(30) Foreign Application Priority Data

Mar. 13, 2023 (TW) ................................. 112109135

(51) Int. Cl.
| | |
|---|---|
| *A61K 38/48* | (2006.01) |
| *A61K 36/28* | (2006.01) |
| *A61P 1/00* | (2006.01) |
| *A61P 29/00* | (2006.01) |

(52) U.S. Cl.
CPC .......... *A61K 38/4873* (2013.01); *A61K 36/28* (2013.01); *A61P 1/00* (2018.01); *A61P 29/00* (2018.01)

(58) Field of Classification Search
None
See application file for complete search history.

(56) References Cited

U.S. PATENT DOCUMENTS

2007/0053998 A1* 3/2007 Yang .......................... A61P 3/10
424/725
2017/0319642 A1* 11/2017 Bozinis ................ A61K 9/2031

OTHER PUBLICATIONS

Silva et al., "Compilation of Secondary Metabolites from *Bidens pilosa* L", Molecules, vol. 16, pp. 1070-1102 (Year: 2011).*
Bottega et al., "Anti-inflammatory properties of a proprietary bromelain extract (Bromeyal) after in vitro stimulated gastrointestinal digestion", International Journal of Immunopathology & Pharmacology, vol. 35, pp. 1-9 (Year: 2021).*
Laura P. Hale et al., Treatment with oral bromelain decreases colonic inflammation in the IL-10-deficient murine model of inflammatory bowel disease, Clinical Immunology 116 (2005) 135-142.
Ana E. V. Quagilo et al., *Bidens pilosa* (Black Jack) Standardized Extract Ameliorates Acute TNBS-induced Intestinal Inflammation in Rats, Planta Med . Mar. 2020;86(5):319-330. doi: 10.1055/a-1089-8342. Epub Jan. 30, 2020.
Yu-Lan Li et al.,Flavonoids and a New Polyacetylene from Bidens parviflora Willd., Molecules 2008, 13, 1931-1941, Published: Aug. 28, 2008.
[0039] Shih-Chang Chien et al., Anti-diabetic properties of three common Bidens pilosa variants in Taiwan, Phytochemistry, Jul. 2009; 70(10):1246-54, Epub Aug. 14, 2009.

* cited by examiner

*Primary Examiner* — Michelle F. Paguio Frising
(74) *Attorney, Agent, or Firm* — MUNCY, GEISSLER, OLDS & LOWE, P.C.

(57) ABSTRACT

A method for treating and/or improving inflammatory intestinal disease includes administering a composition to a patient suffering from inflammatory intestinal disease to be capable of effectively inhibiting the patient's intestinal bleeding, intestinal inflammation, and capable of achieving efficacies of repairing intestinal cells and intestinal wall structure. The composition contains an effective amount of bromelain and/or an effective amount of *Bidens pilosa* extract.

5 Claims, 6 Drawing Sheets

METHOD FOR TREATING AND/OR IMPROVING INFLAMMATORY INTESTINAL DISEASE

FIELD OF THE INVENTION

The invention relates to a treatment method for intestinal inflammatory disease, and more particularly to a method for treating and/or improving inflammatory intestinal disease.

DESCRIPTION OF THE RELATED ART

Inflammatory intestinal disease (IBD) is a disease that includes several inflammatory symptoms of the digestive system, it is mainly divided into two types, one of which is ulcerative colitis and the other is Crohn's disease. Inflammatory intestinal disease will cause the patient's intestinal tract in an inflammatory state for a long period of time, and symptoms such as ulcer, inflammation, bleeding will appear on the intestinal wall, and the patient will frequently suffer from symptoms such as diarrhea and feces bleeding, which will cause extreme inconvenience in life; in addition, besides digestive tract symptoms, it may also cause diseases such as eye inflammation, skin diseases, and arthritis.

At present, most clinical treatment methods for inflammatory intestinal disease are symptomatic treatment with drugs, such as anti-inflammatory drugs, antibiotics, antidiarrheal drugs, and the like, but there is no radical cure effect on inflammatory intestinal disease. Recently, biological agents have been used for treatment; however, although biological agents can improve the clinical symptoms of most patients, in fact intestinal inflammation and ulcer symptoms of about 70% of patients continue to occur. In other words, biological agents still cannot achieve efficacies of repairing the intestinal tract and treating the disease at the same time.

SUMMARY OF THE INVENTION

A main object of the invention is to provide a method for treating and/or improving inflammatory intestinal disease not only capable of improving the symptoms of inflammatory intestinal disease, but also capable of effectively repairing damaged intestinal cells to be capable of using as of a therapeutic drug or as an adjuvant or a nutritional supplement to assist in clinical treatment.

Another object of the invention is to provide a method for treating and/or improving inflammatory intestinal disease, since a main active ingredient in an administered composition comes from natural plant extract, long-term administration will not have adverse effects on human health.

In order to achieve the above objects, the invention discloses a method for treating and/or improving inflammatory intestinal disease, comprising administering a composition to a patient suffering from inflammatory intestinal disease, wherein the composition contains an effective amount of bromelain and/or an effective amount of *Bidens pilosa* extract. The method for treating and/or improving inflammatory intestinal disease disclosed by the invention is capable of effectively repairing damaged intestinal cells of a patient, inhibiting intestinal bleeding, and restoring intestinal structure to achieve efficacies of treating or improving inflammatory intestinal disease and its symptoms.

In one embodiment of the invention, the active ingredient of the composition is the bromelain.

In another embodiment of the invention, the active ingredient of the composition is the *Bidens pilosa* extract.

In another embodiment of the invention, the composition contains the bromelain and the *Bidens pilosa* extract.

In yet another embodiment of the invention, the composition is composed of the bromelain and the *Bidens pilosa* extract.

In one embodiment of the invention, the method for treating and/or improving inflammatory intestinal disease further comprises administering a clinical drug to the patient, wherein the clinical drug is used for improving symptoms of inflammatory intestinal disease, and the composition is used for repairing damaged intestinal structure and restoring intestinal cells to normal. Thereby, administering the clinical drug and the composition of this invention to the patient at the same time is capable of achieving an efficacy of improving a therapeutic effect of inflammatory intestinal disease.

In one embodiment of the invention, the composition can be prepared as a food, a medicine, or an adjuvant.

In one embodiment of the invention, the bromelain is an enzyme with broad-spectrum protein hydrolysis function. Generally speaking, the bromelain can be extracted from bromeliad plants, and can also be purchased from the market.

In one embodiment of the invention, the *Bidens pilosa* extract is obtained from *Bidens pilosa* through an extraction procedure, and its main ingredients are flavonoids, such as centaurein, centaureidin, and the like, wherein an extraction solvent used in the extraction procedure is a pharmaceutically or food acceptable solvent, such as water, lower alcohols, and the like.

DETAILED DESCRIPTION OF THE INVENTION

Figure 1:
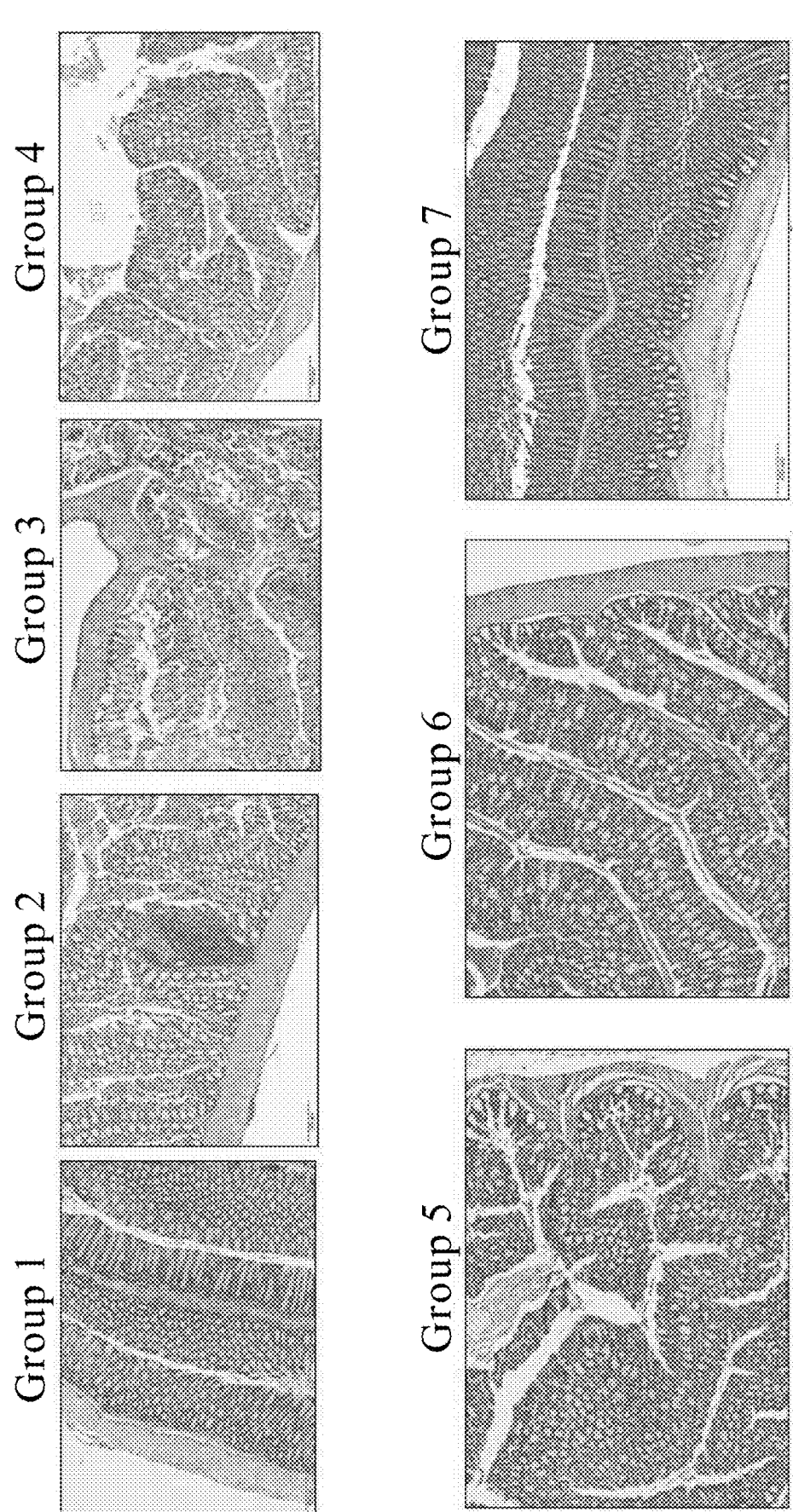
FIG. 1 shows H&E staining diagrams of longitudinal sections of anterior intestinal tracts of mice in each group.

The invention provides a method for treating and/or improving inflammatory intestinal disease, comprising administering a composition to a patient suffering from inflammatory intestinal disease to be capable of effectively inhibiting the patient's intestinal bleeding, intestinal inflammation, and capable of achieving efficacies of repairing intestinal cells and intestinal wall structure, wherein the pharmaceutical composition contains an effective amount of bromelain and/or an effective amount of *Bidens pilosa* extract.

In one embodiment of the invention, the composition contains the bromelain and the *Bidens pilosa* extract.

In another embodiment of the invention, the composition is composed of the bromelain and the *Bidens pilosa* extract, and the bromelain and the *Bidens pilosa* extract are produced by mixing according to a predetermined ratio.

In one embodiment of the invention, the bromelain is stem bromelain (SBM; EC 3.4.22.32), which is a proteolytic enzyme extracted from pineapple stem, and its CAS number is 37189-34-7.

In one embodiment of the invention, main ingredients of the *Bidens pilosa* extract are flavonoids, such as centaurein, centaureidin and the like.

For example, the *Bidens pilosa* extract disclosed in the invention is prepared according to the following method: after grinding fresh whole herb of *Bidens pilosa* (1.2 kg), extraction is carried out with boiling water (9 L×2) to obtain the *Bidens pilosa* extract. Main active ingredients contained in the *Bidens pilosa* extract are identified as flavonoid compounds, including centaurein, centaureidin, and the like, through the principle of biological activity separation (BGFI) and column analysis technology. In addition to using fresh whole herb of *Bidens pilosa* for extraction mentioned above, the leaves of *Bidens pilosa* can also be used for extraction, wherein an extraction solvent can be lower alcohols, and the *Bidens pilosa* extract disclosed in the invention can also be obtained.

In yet another embodiment of the invention, the method for treating and/or improving inflammatory intestinal disease further comprises administering a clinical drug to the individual, wherein the clinical drug is a drug used for treating inflammatory intestinal disease in accordance with the clinical drug guidelines. In other words, the composition disclosed in the invention can be used as an adjuvant for treating inflammatory intestinal disease.

The bromelain disclosed in the invention is a proteolytic enzyme, which is an enzyme extracted from stems, fruits, leaves and other parts of bromeliad plants.

The *Bidens pilosa* extract disclosed in the invention is obtained by extracting and separating *Bidens pilosa*, wherein the so-called extraction procedure is well known to a person having ordinary skill in the art to which the invention pertains and is an extraction technique acceptable in pharmaceutical applications.

The composition disclosed in the invention contains an effective amount of plant extract, and the plant extract is bromelain and/or *Bidens pilosa* extract. The composition can be a food, an adjuvant, or a drug, and a pharmaceutically or food acceptable carrier can be added, and a dosage form or a form such as liquid, lozenge, powder, and the like can be changed according to parameters such as use requirements, purposes, and administration objects.

"Existing clinical drug", "clinical drug" or "pharmaceutical composition conforming to conventional practices of treatment of inflammatory intestinal disease" disclosed in the invention refers to a drug used for treating inflammatory intestinal disease in accordance with the clinical drug guidelines, including antidiarrheal drugs, anti-inflammatory drugs, antibiotics, immunomodulators, anti-parasympathetic antispasmodics, H2 receptor antagonists, hydrogen ion pump inhibitors, steroids, and the like.

Numerical range disclosed in the invention should be interpreted as including not only numerical values explicitly listed, but also reasonable and effective numerical values acceptable to a person having ordinary skill in the art to which the invention pertains.

Wherein the so-called effective amount refers to an amount that can be used on an individual to produce an effect of preventing, treating, improving, or alleviating worsening of a disease or its symptoms; in the experimental examples disclosed in the invention, since the subjects used are mice, if the administered individual is a 60 kg adult, it is required to convert a mouse dose to an adult dose according to the general knowledge of the invention.

In the following, in order to illustrate the technical features and applications of the invention, several examples are specifically proposed and described in detail with accompanying drawings hereinafter.

Experimental animals used in the following examples are BALB/c strain mice purchased from the National Laboratory Animal Center (NLAC) as an incorporated foundation. The mice are reared with standard feed and drinking water, and have 12-hour light adjustment. All the experimental animals are approved by the Experimental Animal Committee of Tunghai University in Taiwan.

The "TNBS" (2,4,6-Trinitrobenzenesulfonic acid) used in the following examples is a corrosive agent, which is a drug commonly used by a person having ordinary skill in the art to which the invention pertains to induce animals to form an acute colitis model. In many documents, an animal model of inflammatory intestinal disease induced by TNBS is also adopted.

The bromelain used in the following examples is stem bromelain (SBM; EC 3.4.22.32) prepared by an advanced manufacturing process, and its CAS number is 37189-34-7, which is an enzyme with broad-spectrum proteolytic properties.

The *Bidens pilosa* extract used in the following examples is prepared with reference to the following documents, and its main ingredients are centaurein and centaureidin:

Shih-Chang Chien et al, Anti-diabetic properties of three common *Bidens pilosa* variants in Taiwan, Phytochemistry, 2009 July; 70 (10): 1246-54, Epub 2009 Aug. 14.

The content of the following examples should not be interpreted as a limitation of the disclosure content of this specification and a scope of protection claimed by the invention, especially a dose of the bromelain and the *Bidens pilosa* extract in the following examples; a person having ordinary skill in the art to which the invention pertains is capable of adjusting a dose according to different administered species.

Example 1: Construction of an Animal Model of Acute Enteritis

Dissolve 30 mg/kg of TNBS (trinitrobenzene sulfonic acid) in 0.25 L of 25% alcohol, and administer it rectally to BALB/c strain mice to induce acute enteritis in the mice and become acute enteritis model mice.

Example 2: Animal Experiment

Several BALB/c strain mice are randomly divided into seven groups, wherein the mice in the 3rd to 7th groups are induced into acute enteritis model mice with TNBS on the 0th day of the experiment, and the mice in each of the groups are treated with the following conditions:

Group 1: normal control group without any treatment;

Group 2: Administer 0.25 mL of 25% alcohol (without TNBS) rectally;

Group 3: Mice with acute enteritis induced by TNBS;

Group 4: Mice with acute enteritis induced by TNBS, and administer Mesalazine daily from day 1 to day 7 of the experiment, with a dose of 53.34 mg/kg (0.05334 mg/g);

Group 5: Mice with acute enteritis induced by TNBS, and administer the bromelain daily from day 1 to day 7 of the experiment, with a dose of 133.34 mg/kg (0.134 mg/g);

Group 6: Mice with acute enteritis induced by TNBS, and administer the *Bidens pilosa* extract daily from day 1 to day 7 of the experiment, with a dose of 50 mg/kg (0.05 mg/g)

Group 7: Mice with acute enteritis induced by TNBS, and administer the composition disclosed by the invention daily from day 1 to day 7 of the experiment, wherein the composition contains the bromelain and the *Bidens pilosa* extract, a dose of the bromelain is 133.34 mg/kg (0.134 mg/g), and a dose of the *Bidens pilosa* extract is 50 mg/kg (0.05 mg/g).

Figure 2:
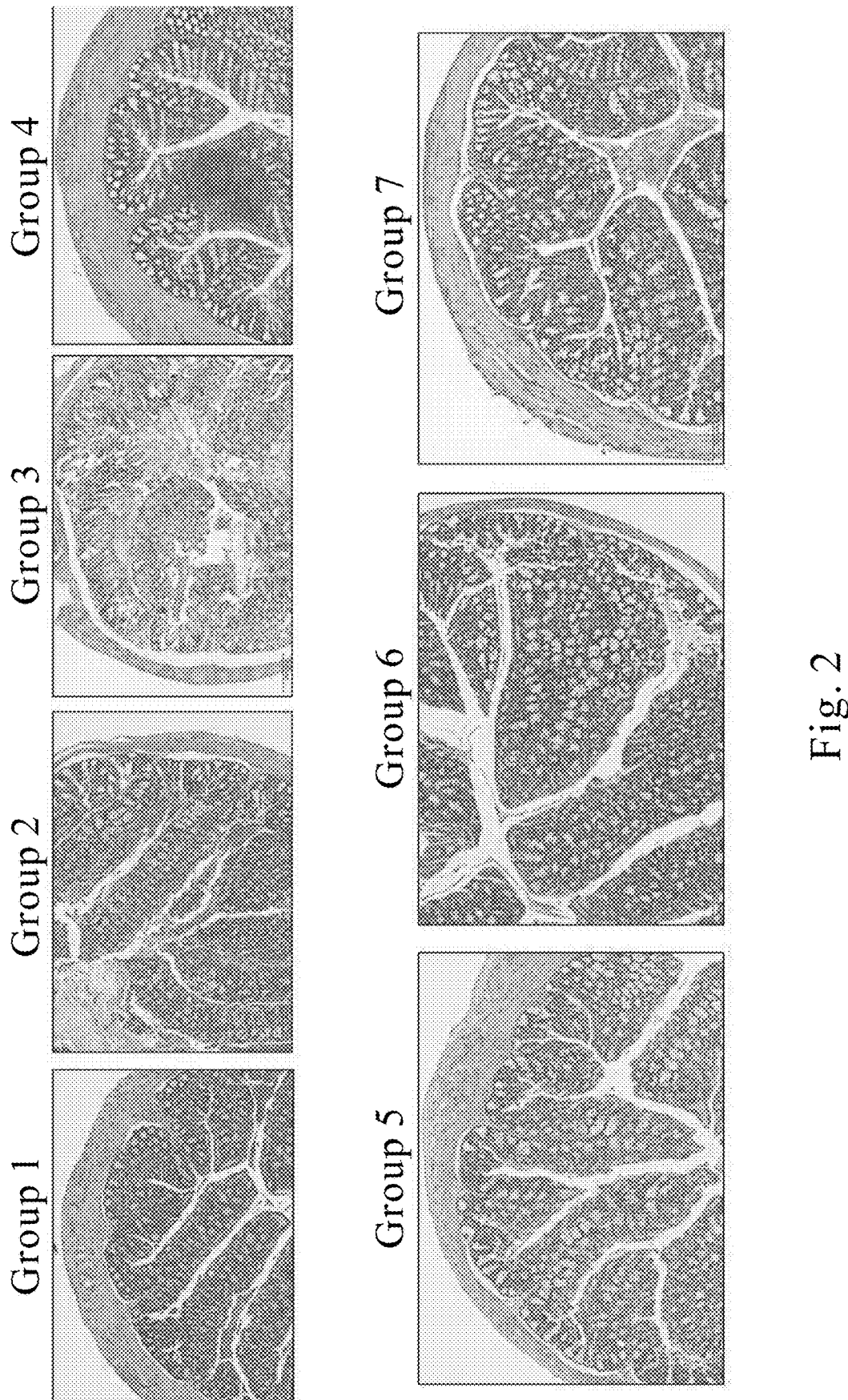
FIG. 2 shows H&E staining diagrams of transverse sections of anterior intestinal tracts of the mice in each of the groups.
Figure 3:
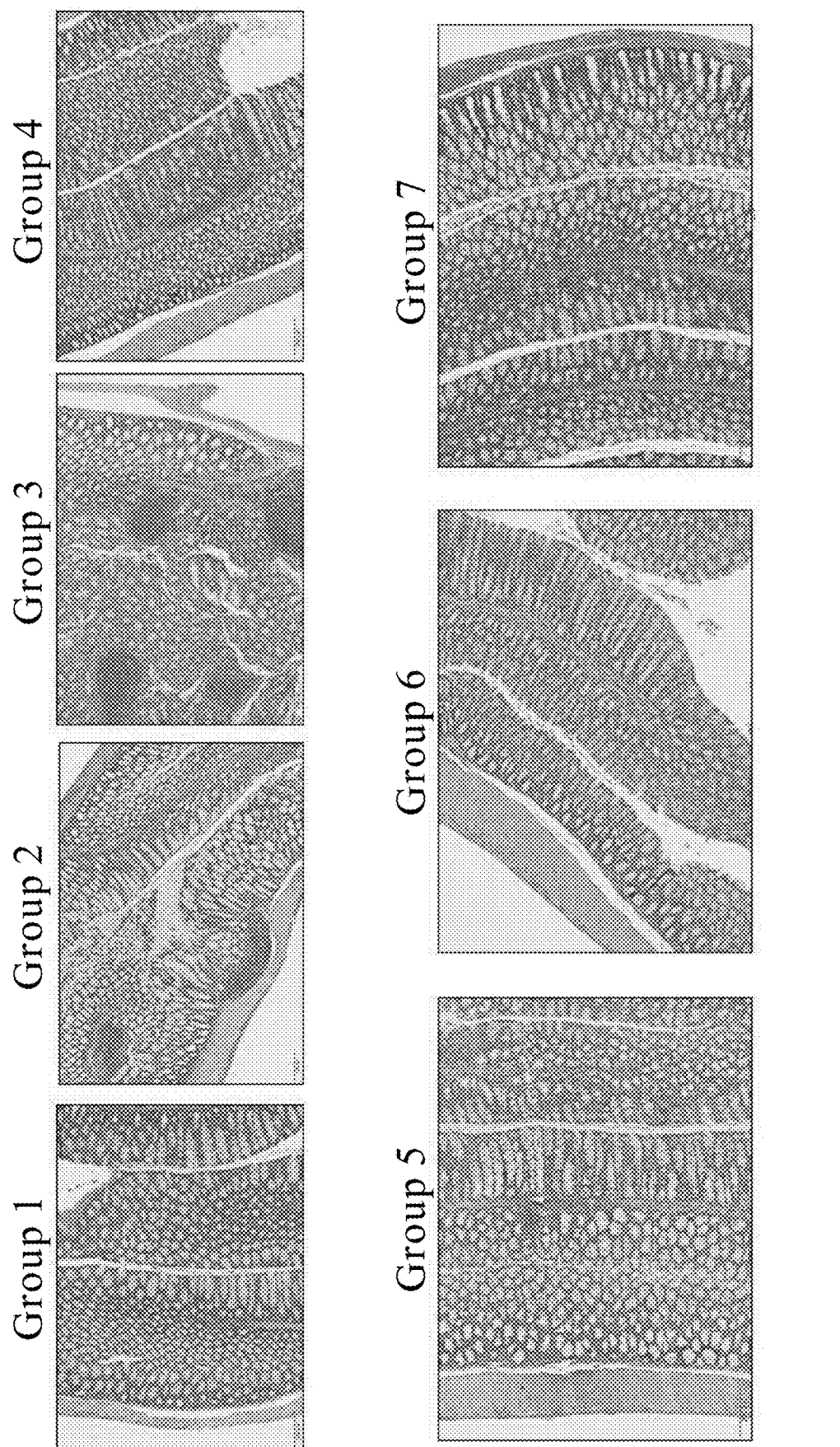
FIG. 3 shows H&E staining diagrams of longitudinal sections of middle intestinal tracts of the mice in each of the groups.
Figure 4:
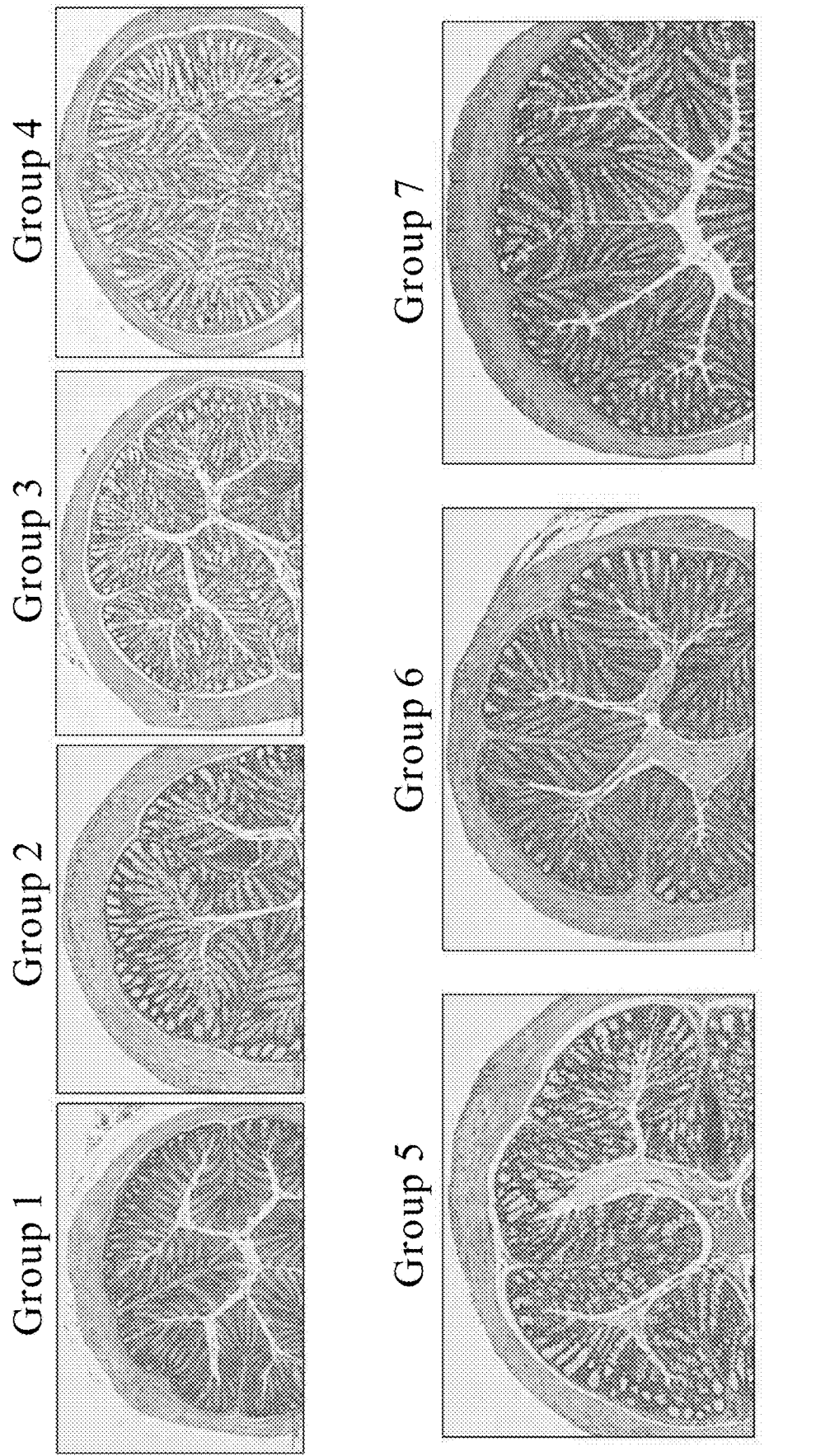
FIG. 4 shows H&E staining diagrams of transverse sections of middle intestinal tracts of the mice in each of the groups.
Figure 5:
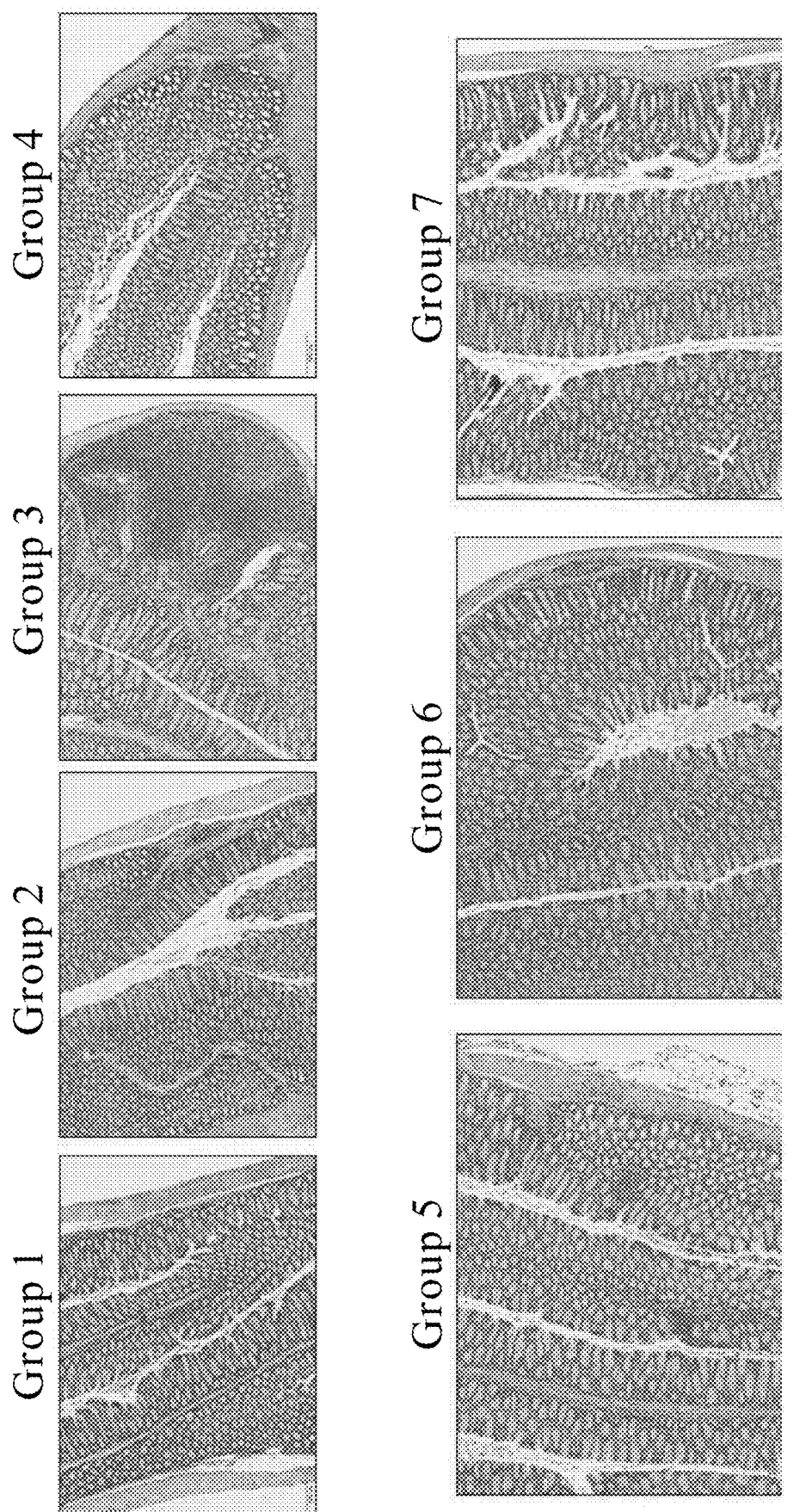
FIG. 5 shows H&E staining diagrams of longitudinal sections of posterior intestinal tracts of the mice in each of the groups.
Figure 6:
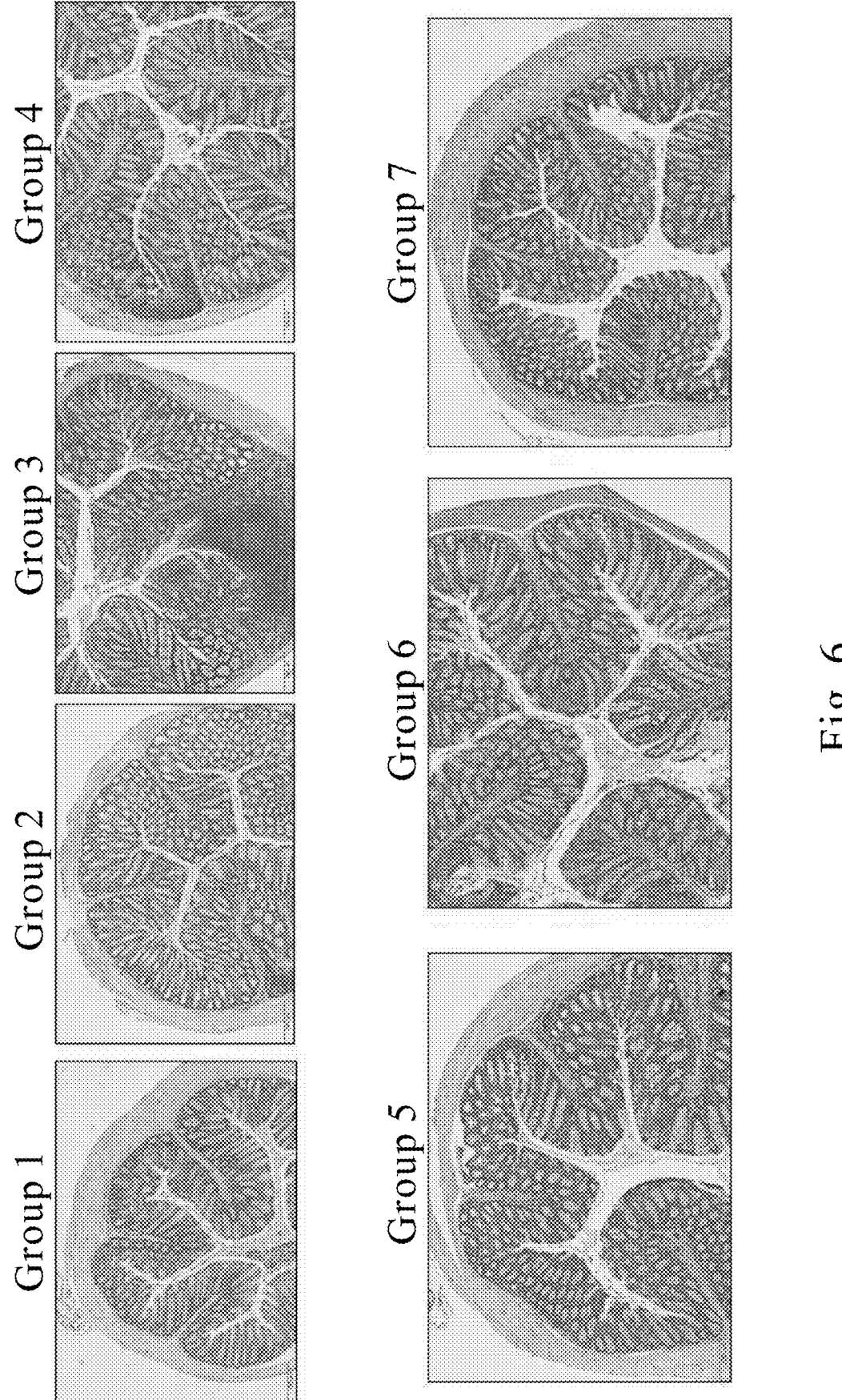
FIG. 6 shows H&E staining diagrams of transverse sections of posterior intestinal tracts of the mice in each of the groups.

The mice in each of the groups are sacrificed on the 8th day of the experiment, and then intestinal tissues of the mice in each of the groups are collected for appearance evaluation and tissue section staining analysis. The results are shown in FIGS. 1 to 6.

From the results in FIG. 1 to FIG. 6, it can be known that structures of intestinal tracts of the mice in group 3 are seriously damaged, thicknesses of intestinal walls are abnormally thickened and swollen, mucosal tissues are ulcerated and bleeding, structures of crypts are atrophied, distorted and branched, leukocytes/lymphocytes are infiltrated and have severe inflammation, crypt mitochondria are atrophied, and mucus disappearance in goblet cells; compared with the intestinal state of the mice in the first group and the second group, it shows that acute enteritis model mice could indeed be successfully induced by administering the TNBS.

Furthermore, comparing the intestinal sections of the mice in group 4 with the intestinal sections of the mice in group 1, it can be known that although administration of Mesalazine, a drug clinically used to treat enteritis, can improve the symptoms of leukocytes/lymphocytes infiltration and severe inflammation in the intestinal tract, intestinal bleeding still continues and a thickness of the intestinal tract is still thick, indicating that administering clinical drugs, such as Mesalazine, to individuals suffering from acute enteritis can only improve symptoms related to inflammation, but is unable to achieve efficacies of repairing intestinal structure and inhibiting bleeding.

Further, the results of comparing the stained intestinal sections of the mice from groups 3 to 7 with those of the mice in group 1 are listed in Table 1 below. From the results in Table 1, it can be known that compared with the mice in group 3, the intestinal structure, inflammation symptoms and bleeding symptoms of the mice in the 5th to 7th groups tend to recover. Wherein compared with the mice in group 1, although the intestinal walls of the mice in the fifth group are still relatively thickened, the inflammation and bleeding phenomena are significantly improved, while thicknesses of the intestinal walls of the mice in the sixth group not only restore to normal, but also the bleeding and inflammation phenomena are significantly improved, but in contrast to the mice in group 7, the intestinal structure, thickness and function not only restore to normal, bleeding symptoms are also inhibited, and inflammation symptoms are significantly improved.

TABLE 1

| Characteristic analysis of stained sections of intestinal tissues of the mice in each of the groups |
| --- |
| Characteristics of Stained Sections of intestinal Tissues |

| Group | Characteristics |
| --- | --- |
| Group 1 | The structure is closely arranged; thin intestinal wall thickness; mucosal tissues are intact without bleeding spot; structures of crypts are intact; no inflammatory symptoms such as leukocytes/lymphocytes infiltration; there are a large number of goblet cells and can secrete mucus normally. |
| Group 3 | Severe structural damage; abnormally thickened, swollen, or damaged intestinal wall thickness; mucosal tissues are ulcerated and bleeding; structures of crypts are atrophied, distorted and branched; leukocytes/lymphocytes are infiltrated and have severe inflammation; crypt mitochondria are atrophied; mucus disappearance in goblet cells |
| Group 5 | The structure is arranged relatively intact; intestinal wall thickness is thickened; mucosal tissues are intact with some bleeding spots; structures of crypts are atrophied, distorted and branches with inflammatory symptoms such as local leukocytes/lymphocytes infiltration; some goblet cells can secrete mucus normally, but some goblet cells are still abnormal. |
| Group 6 | The structure is arranged relatively intact; intestinal wall thickness restores thinness; mucosal tissues are intact with some bleeding spots; structures of crypts are atrophied, distorted and branches with inflammatory symptoms such as local leukocytes/lymphocytes infiltration; some goblet cells can secrete mucus normally, but some goblet cells are still abnormal. |
| Group 7 | The structure is closely arranged and intact; intestinal wall thickness restores thinness; some mucosal tissues restore to be intact without obvious bleeding spots; structures of crypts are intact; only local leukocytes/lymphocytes have symptoms of infiltration and inflammation; a large number of goblet cells restore to normal and can secrete mucus normally. |

From the above results, it can be known that administering an effective amount of the bromelain, an effective amount of the *Bidens pilosa* extract, or a combination of the above two extracts to an individual suffering from inflammatory intestinal disease is capable of improving inflammatory symptoms caused by inflammatory intestinal disease, and further capable of repairing damaged intestinal cells, effectively inhibiting bleeding, restoring structure and thickness of an intestinal tract to normal to be capable of causing the intestinal tract to perform its normal functions to achieve efficacies of treating, improving or alleviating inflammatory intestinal disease.

It can be known that, compared with clinical medication, the composition disclosed in the invention is not only for symptomatic treatment, but is capable of repairing and improving damaged intestinal tissues. Therefore, the composition disclosed in the invention can be used as a drug for treating or improving inflammatory intestinal disease, and can also be used as an adjuvant or a dietary supplement in combination with existing clinical drugs to achieve an efficacy of accelerating recovery of patients.

Although the invention has been disclosed as above with the embodiments, it is not intended to limit the invention. A person having ordinary skill in the art to which the invention pertains can make various changes and modifications without departing from the spirit and scope of the invention. Therefore, scope of protection of the invention shall be subject to what is defined in the pending claims.

What is claimed is:

1. A method for treating and/or improving inflammatory intestinal disease and bleeding thereof, comprising administering a composition to a patient suffering from inflammatory intestinal disease, wherein the composition is capable of effectively inhibiting the patient's intestinal bleeding and repairing intestinal cells, wherein the composition contains an effective amount of bromelain and an effective amount of *Bidens pilosa* extract;

wherein the bromelain is stem bromelain with a CAS number of 37189-34-7, and the *Bidens pilosa* extract includes centaurein and centaureidin.

2. The method for treating and/or improving inflammatory intestinal disease and bleeding thereof as claimed in claim 1, wherein the composition is composed of the bromelain and the *Bidens pilosa* extract.

3. The method for treating and/or improving inflammatory intestinal disease and bleeding thereof as claimed in claim 1, further comprising administering a drug to the individual, wherein the drug is a pharmaceutical composition conforming to conventional practices of treatment of inflammatory intestinal disease.

4. The method for treating and/or improving inflammatory intestinal disease and bleeding thereof as claimed in claim 1, wherein the bromelain is obtained by performing an extracting procedure on a stem of a bromeliad plant.

5. The method for treating and/or improving inflammatory intestinal disease and bleeding thereof as claimed in claim 1, wherein active ingredients of the *Bidens pilosa* extract are flavonoids.

* * * * *